(12) United States Patent
Farrand et al.

(10) Patent No.: US 7,442,475 B2
(45) Date of Patent: Oct. 28, 2008

(54) CYANOPYRIDONE DERIVATIVES AS LIQUID CRYSTALS

(75) Inventors: Louise Diane Farrand, Dorset (GB); Michael Heckmeier, Hemsbach (DE)

(73) Assignee: Merck Patent GmbH, Darmstadt (DE)

( * ) Notice: Subject to any disclaimer, the term of this patent is extended or adjusted under 35 U.S.C. 154(b) by 347 days.

(21) Appl. No.: 10/546,146

(22) PCT Filed: Jan. 23, 2004

(86) PCT No.: PCT/EP2004/000552

§ 371 (c)(1), (2), (4) Date: Aug. 22, 2005

(87) PCT Pub. No.: WO2004/074253

PCT Pub. Date: Sep. 2, 2004

(65) Prior Publication Data

US 2006/0165916 A1    Jul. 27, 2006

(30) Foreign Application Priority Data

Feb. 22, 2003 (EP) .................................. 03003968

(51) Int. Cl.
G03C 19/00 (2006.01)
G03C 19/52 (2006.01)

(52) U.S. Cl. ................ 430/20; 430/270.1; 252/299.01; 428/1.1; 428/1.2

(58) Field of Classification Search ............. 430/20, 430/270.1; 252/299.01; 428/1.1, 1.2
See application file for complete search history.

(56) References Cited

U.S. PATENT DOCUMENTS

| 4,684,477 A | 8/1987 | Nigorikawa et al. |
| 4,983,609 A | 1/1991 | Fuji et al. |
| 6,664,025 B2 * | 12/2003 | Baumann et al. ......... 430/270.1 |

FOREIGN PATENT DOCUMENTS

| EP | 0 180 188 | 5/1986 |
| EP | 0 194 153 | 9/1986 |
| EP | 0 310 676 | 4/1989 |
| JP | 04 217665 | 8/1992 |

OTHER PUBLICATIONS

Database CA 'Online! Chemical Abstracts Service, Columbus, Ohio, US; Pavelyuchenko, A.I.et al: "Synthesis and Liquid-Crystal Properties of 2-(4-Alkyl-or 4-Alkoxyphenyl) -5-Cyanopyridines" Retrieved From STN Database Accession No. 106:156234.

\* cited by examiner

*Primary Examiner*—Geraldina Visconti
(74) *Attorney, Agent, or Firm*—Millen, White, Zelano, Branigan, P.C.

(57) ABSTRACT

The invention relates to cyanopyridone derivatives, to their use in liquid crystal media, liquid crystal devices, anisotropic polymers, optical, electrooptical, decorative, security, cosmetic, diagnostic, pharmaceutic, electric, electronic, charge transport, semiconductor, optical recording, electroluminescent, photoconductor and electrophotographic applications, and to liquid crystal media, polymers and displays comprising them.

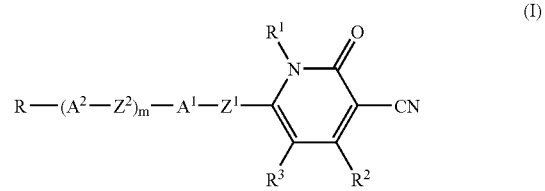

19 Claims, No Drawings

CYANOPYRIDONE DERIVATIVES AS LIQUID CRYSTALS

FIELD OF THE INVENTION

The invention relates to cyanopyridone derivatives, to their use in liquid crystal media, liquid crystal devices, anisotropic polymers, optical, electrooptical, decorative, security, cosmetic, diagnostic, pharmaceutic, electric, electronic, charge transport, semiconductor, optical recording, electroluminescent, photoconductor and electrophotographic applications, and to liquid crystal media, polymers and displays comprising them.

BACKGROUND AND PRIOR ART

For use in liquid crystal display (LCD) applications it is often required to have available liquid crystal (LC) compounds and media with a high positive value of the dielectric anisotropy $\Delta\epsilon$, which in turn requires that the material has a large molecular dipole. Until now, materials with terminal cyano groups have been used extensively for this purpose, as the cyano group is of high polarisability.

Thus, LC compounds with a $\Delta\epsilon$ of +20 or more and having a terminal cyano group are widely known in prior art. For many applications, however, LC compounds and media with still higher $\Delta\epsilon$ are needed. Furthermore, the compounds known from prior art do often have unfavourable properties, like high melting points, smectic phases or unfavourable vaues of the birefringence.

Consequently, there is still a need for materials with high polarity and positive $\Delta\epsilon$ that can be used in LC media to increase the value of $\Delta\epsilon$, without negatively affecting the other properties of the media, such as the LC phase range.

The inventors of the present invention have found that the above mentioned drawbacks can be overcome by providing cyanopyridone derivatives as claimed in the present invention. These compounds have advantageous properties and are suitable for use in optical, electrooptical, security, electronic, charge transport, semiconductor, optical recording, electroluminescent, photovoltaic or electrophotographic applications, in particular in LC media and LC devices.

WO 88/07992 describes 5-cyano-1,6-dihydro-6-oxo-2-(4-octyloxyphenyl)-pyridine as intermediate in the preparation of cyanopyridines for ferroelectric LC media.

EP 0 180 188 describes the use of 3,4,5-trimethoxybenzoic acid 5-cyano-1,6-dihydro-6-oxo-2-pyridinyl ester for use in pharmaceutic compositions to increase the anticancer activity of 3-fluorouracil and related compounds.

DeJohn et al., J. Heterocycl. Chem. 1983, 20(5), 1295-1302 describe 5-cyano-1,6-dihydro-6-oxo-2-[2-(4-methoxyphenyl)ethenyl]pyridine. Rateb et al., J. Chem Soc. 1960, 1426-1430 describe 3-cyano-1,2-dihydro-6-(4-methoxystyryl)-2-oxo-isonicotinic acid ethyl ester and its substituted derivatives.

One aim of the present invention is to provide novel cyanopyridone derivatives with improved properties, especially mesogenic or liquid crystalline cyanopyridones with a rod-shaped molecular structure and polymerisable cyanopyridones.

Another aim is to provide advantageous uses for the novel cyanopyridone derivatives, such as liquid crystal media, liquid crystal devices, anisotropic polymers, optical, electrooptical, decorative, security, cosmetic, pharmaceutic, diagnostic, electric, electronic, charge transport, semiconductor, optical recording, electroluminescent, photoconductor and electrophotographic applications.

Another aim of the invention is to provide improved LC media and LC polymers with high polarity and high positive values of the dielectric anisotropy that do not have the drawbacks of LC media known from prior art.

Other aims of the present invention are immediately evident to the person skilled in the art from the following detailed description.

SUMMARY OF THE INVENTION

The invention relates to the use of a compound comprising at least one 5-cyanopyridon-2-yl group (cyanopyridone derivative) as mesogenic or liquid crystalline material, in liquid crystal media, liquid crystal devices, anisotropic polymers, optical, electrooptical, decorative, security, cosmetic, diagnostic, electric, electronic, charge transport, semiconductor, optical recording, electroluminescent, photoconductor and electrophotographic applications.

The invention further relates to the use of a compound comprising at least one 5-cyanopyridon-2-yl group for the applications described above, wherein the 5-cyanopyridon-2-yl group is selected of formula (1)

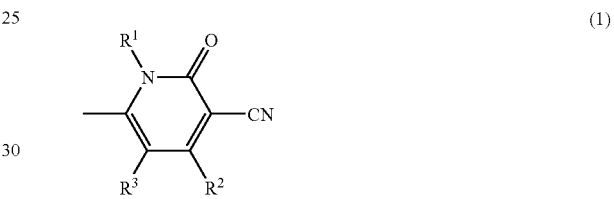

wherein $R^1$, $R^2$ and $R^3$ are independently of each other H or an optionally substituted aliphatic, cycloaliphatic or aromatic group with up to 20 C atoms that optionally comprises one or more hetero atoms and optionally comprises fused rings.

The invention further relates to the uses as described above, wherein the cyanopyridone derivative is selected of formula I

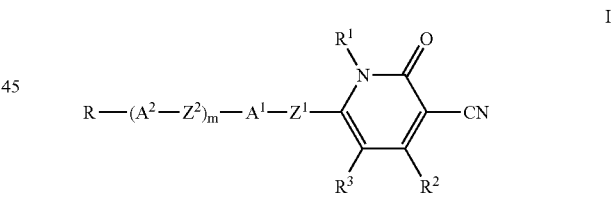

wherein $R^1$, $R^2$ and $R^3$ are as defined in formula (1), $A^1$ and $A^2$ are independently of each other an aromatic or alicyclic ring, or a group comprising two or more fused aromatic or alicyclic rings, wherein these rings optionally contain one or more hetero atoms selected from N, O and S, and are optionally mono- or polysubstituted by R, $Z^1$ and $Z^2$ are independently of each other —O—, —S—, —CO—, —COO—, —OCO—, —S—CO—, —CO—S—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, $Y^1$ and $Y^2$ are independently of each other H, F, Cl or CN, R is H, F, Cl, Br, I, CN, $NO_2$, NCS, $SF_5$ or alkyl which is straight chain or branched, has 1 to 20 C-atoms, is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —$CY^1$=$CY^2$— or —C≡C— in such a manner that O and/or S atoms are not linked directly to one another, or R denotes P-Sp, $R^0$ and $R^{00}$ are independently of each other H or alkyl with 1 to 12 C-atoms, P is a polymerisable or reactive group, Sp is a spacer group or a single bond, and m is 0, 1 or 2.

The invention further relates to mesogenic or liquid crystalline cyanopyridone derivatives, in particular compounds comprising at least one group of formula (1) as defined above.

The invention further relates to novel cyanopyridone derivatives of formula I, in particular to mesogenic or liquid crystalline cyanopyridone derivatives of formula I

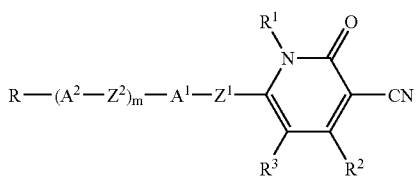

I wherein $A^1$, $A^2$, $Z^1$, $Z^2$, R, $R^1$, $R^2$, $R^3$ and m are as defined above, with the provisos that a) if m is 0, $R^1$, $R^2$ and $R^3$ are H and $Z^1$ is a single bond, then $A^1$-R is different from 4-alkylphenyl or 4-alkoxyphenyl, b) if m is 0, $R^1$, $R^2$ and $R^3$ are H and $Z^1$ is COO or CH=CH, then $A^1$-R is different from 4-methoxyphenyl, 3,4-dimethoxyphenyl or 3,4,5-trimethoxyphenyl, c) if m is 0, $R^1$ and $R^3$ are H, $R^2$ is carboxyethyl and $Z^1$ is CH=CH, CH=C($CH_3$) or CH=C($C_6H_5$), then $A^1$-R is different from phenyl or 4-methoxyphenyl.

The invention further relates to an LC medium comprising at least one cyanopyridone derivative which preferably comprises at least one group of formula (1) and is very preferably selected of formula I.

The invention further relates to a polymerisable LC medium comprising at least one cyanopyridone derivative and at least one polymerisable compound, wherein said cyanopyridone derivative preferably comprises at least one group of formula (1) and is very preferably selected of formula I, and said polymerisable compound can be said cyanopyridone derivative or an additional compound.

The invention further relates to a polymer obtained by polymerising a cyanopyridone derivative or a polymerisable LC medium as described above and below.

The invention further relates to an anisotropic polymer obtained by polymerising a cyanopyridone derivative or a polymerisable LC medium as described above and below in its oriented state, preferably in form of a film.

The invention further relates to the use of a cyanopyridone derivative, a liquid crystal medium, a polymer or a polymer film as described above and below in electrooptical displays, liquid crystal displays, optical films, polarisers, compensators, beam splitters, reflective films, alignment layers, colour filters, holographic elements, hot stamping foils, coloured images, decorative or security markings e.g. for consumer objects or documents of value, LC pigments, adhesives, synthetic resins with anisotropic mechanical properties, cosmetics, pharmaceutics, diagnostics, nonlinear optics, optical information storage, as chiral dopants, in electronic devices like for example field effect transistors (FET) as components of integrated circuitry, as thin film transistors in flat panel display applications or for Radio Frequency Identification (RFID) tags, or in semiconducting components for organic light emitting diode (OLED) applications, electroluminescent displays or backlights of LCDs, for photovoltaic or sensor devices, as electrode materials in batteries, as photoconductors, or for electrophotographic applications or electrophotographic recording.

The invention further relates to an LC device comprising a cyanopyridone derivative or an LC medium, polymer or polymer film as described above and below.

DEFINITION OF TERMS

The terms 'liquid crystalline or mesogenic material' or 'liquid crystalline or mesogenic compound' means materials or compounds comprising one or more rod-shaped, lath-shaped or disk-shaped mesogenic groups, i.e., groups with the ability to induce LC phase behaviour. The compounds or materials comprising mesogenic groups do not necessarily have to exhibit an LC phase themselves. It is also possible that they show LC phase behaviour only in mixtures with other compounds, or when the mesogenic compounds or materials, or the mixtures thereof, are polymerised.

The terms 'polymerisable' and 'reactive' include compounds or groups that are capable of participating in a polymerisation reaction, like radicalic or ionic chain polymerisation, polyaddition or polycondensation, and reactive compounds or reactive groups that are capable of being grafted for example by condensation or addition to a polymer backbone in a polymeranaloguous reaction.

The term 'film' includes self-supporting, i.e., free-standing, films that show more or less pronounced mechanical stability and flexibility, as well as coatings or layers on a supporting substrate or between two substrates.

DETAILED DESCRIPTION OF THE INVENTION

The LC media and LC devices according to the present invention comprising one or more cyanopyridone derivatives are advantageous as they exhibit an increased dielectric anisotropy Δε.

In particular the novel compounds of formula I are advantageous as they exhibit a very high value of Δε the dielectric anisotropy.

Therefore, it is possible to considerably increase the value of Δε in LC media by using the inventive compounds even in only small amounts.

The cyanopyridone derivatives, in particular the compounds of formula I, are especially useful for a display using liquid crystals in the isotropic state, hereinafter shortly referred to as "isotropic mode display", as described for example in DE 102 172 73 or WO 02/93244 A1. Thus, another object of the present invention is a display of the isotropic mode comprising at least one cyanopyridone derivative, which is preferably a compound of formula I or of the preferred compounds shown above and below, or comprising an LC medium comprising such a cyanopyridone derivative.

Another aspect of the invention relates to polymerisable compounds of formula I, also known as reactive mesogens, and to LC polymers obtained from these compounds or mixtures comprising them.

Another aspect of the invention relates to highly ordered anisotropic LC polymer films that are obtained from polymerisable compounds or reactive mesogens of formula I, or mixtures comprising them, by aligning them in their LC phase into uniform orientation and polymerising them in situ, e.g. by thermal or photopolymerisation.

The novel compounds of formula I have the following advantages
- they are easy to prepare in excellent yield from cheap, commercially available starting materials.
- they are highly polar and, when appropriately substituted, show increased dielectric anisotropy $\Delta\epsilon=\epsilon_{11}-\epsilon_\perp$ due to increased $\epsilon_{11}$.
- they are rod shaped and are suitable as components of LC mixtures in LCDs. The molecules themselves do not necessarily have to exhibit an LC phase, but by being rod shaped they do not diminish the electro-optical properties of the LC host in to which they are dissolved.
- their high polarity is due to the cyano and keto groups at adjacent positions in the ring and gives the compounds high dielectric anisotropy $\Delta\epsilon$.
- they can also be designed to have high birefringence $\Delta n$. High $\Delta\epsilon$ and high $\Delta n$ are desirable properties in LCD applications.
- they can be used to reduce the operating voltage in LCDs, and to modify physical properties of a mixture used for LCDs such as birefringence, viscosity and temperature leading to improvements in optical performance of a display device.
- the presence of an alkyl group on the cyanopyridone ring increases overall polarity of the system by pushing electrons into the ring towards the electron withdrawing cyano constituents. The alkyl substituent also gives rise to smectic phase suppression and also lower melting points. Low melting points are particularly important for compounds in LC mixtures which operate at ambient temperatures.
- they can be polymerised if appropriately substituted.

The compounds of formula I are especially suitable for use in mixtures for LCD applications, in particular for applications using LC mixtures in the nematic or isotropic phase where high birefringence, high polarity and high dielectric anisotropy are required.

Furthermore, the compounds of formula I can be used as reactive mesogens and can be used to make polymers or polymer films for use as optical films, in particular optical retardation or compensation films, alignment layers, colour filters or polarisers in an LCD.

Another field of use of polymerisable compounds of formula I is as semiconductors or charge transport materials. These materials can be used in electronic devices like for example field effect transistors (FET) as components of integrated circuitry, as thin film transistors in flat panel display applications or for Radio Frequency Identification (RFID) tags, or in semiconducting components for organic light emitting diode (OLED) applications, electroluminescent displays or backlights of LCDs, for photovoltaic or sensor devices.

It is also possible to co-polymerise compounds of formula I via group P with other polymerisable mesogenic monomers, as well as with other compounds of formula I, in order to induce or enhance LC phase behaviour.

The LCDs according to the present invention are for example conventional LCDs, in particular those of the DAP (deformation of aligned phases) or VA (vertically aligned) mode, like e.g. ECB (electrically controlled birefringence), CSH (colour super homeotropic), VAN or VAC (vertically aligned nematic or cholesteric) displays, MVA (multi-domain vertically aligned) or PVA (patterned vertically aligned) displays, in displays of the bend mode or hybrid type displays, like e.g. OCB (optically compensated bend cell or optically compensated birefringence), R-OCB (reflective OCB), HAN (hybrid aligned nematic) or pi-cell ($\pi$-cell) displays, furthermore in displays of the TN (twisted nematic), HTN (highly twisted nematic) or STN (super twisted nematic), in AMD-TN (active matrix driven TN) displays, in displays of the IPS (in plane switching) mode which are also known as 'super TFT' displays, or in displays using liquid crystals in the isotropic state, hereinafter shortly referred to as "isotropic mode display", as described for example in DE 102 172 73 and WO 02/93244 A1.

Especially preferred are TN, STN and isotropic mode displays.

The compounds according to the present invention may also be used for applications in the cosmetic, pharmaceutic and diagnostic sector. Possible pharmaceutical applications include for example the use as antineoplastic potentiator in compositions to increase the anticancer activity of 5-fluorouracil or related compounds.

Particularly preferred are compounds of formula I, wherein
$Z^1$ is —O—, —COO—, —OCO—, —OCOO—, —CH$_2$O—, —OCH$_2$—, —CF$_2$O—, —OCF$_2$—, —C≡C— or —CH=CH—, most preferably —COO— or —OCO—, $Z^1$ is different from a single bond, $A^1$ is phenylene that is optionally substituted by one or more groups $R^1$, R is P-Sp-, R is alkyl or alkoxy with 1 to 12, preferably 1 to 8 C-atoms or alkenyl, alkenyloxy or alkinyl with 2 to 12, preferably 2 to 7 C-atoms, Sp is alkylene with 1 to 12 C atoms which is optionally mono- or polysubstituted by F and wherein one or more non-adjacent CH$_2$ may be replaced, in each case independently from one another, by —O—, —CH=CH— or —C≡C—, and that is linked to $A^1$ or $A^2$ via a group selected from —O—, —COO—, —OCO—, —OCOO— and a single bond.

Sp is single bond, m is 0 or 1, $A^1$ and $A^2$ are independently of each other an aromatic or alicyclic ring, preferably a 5-, 6- or 7-membered ring, or a group comprising two or more, preferably two or three, fused aromatic or alicyclic rings, wherein these rings optionally contain one or more hetero atoms selected from N, O and S, and are optionally mono- or polysubstituted with L, wherein L is F, Cl, Br, CN, OH, NO$_2$, or an alkyl, alkoxy, alkylcarbonyl or alkoxycarbonyl group with 1 to 12 C atoms, wherein one or more H atoms are optionally replaced by F or Cl.

L is preferably F, Cl, CN, OH, NO$_2$, CH$_3$, C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$ or OC$_2$F$_5$, in particular F, Cl, CN, CH$_3$, C$_2$H$_5$, OCH$_3$, COCH$_3$ or OCF$_3$, most preferably F, Cl, CH$_3$, OCH$_3$ or COCH$_3$.

Preferred groups $A^1$ and $A^2$ are for example furan, pyrrol, thiophene, oxazole, thiazole, thiadiazole, imidazole, phenylene, cyclohexylene, cyclohexenylene, pyridine, pyrimidine, pyrazine, azulene, indane, naphthalene, tetrahydronaphthalene, anthracene and phenanthrene.

Particularly preferably $A^1$ and $A^2$ are selected from furane-2,5-diyl, thiophene-2,5-diyl, thienothiophene-2,5-diyl, dithienothiophene-2,6-diyl, pyrrol-2,5-diyl, 1,4-phenylene, azulene-2,6-diyl, pyridine-2,5-diyl, pyrimidine-2,5-diyl, naphthalene-2,6-diyl, 1,2,3,4-tetrahydro-naphthalene-2,6-diyl, indane-2,5-diyl, or 1,4-cyclohexylene wherein one or two non-adjacent $CH_2$ groups are optionally replaced by O and/or S, wherein these groups are unsubstituted, mono- or polysubstituted by L as defined above.

Preferably the group $-A^1-(Z^2-A^2)_m-$ contains only monocyclic groups $A^1$ and $A^2$. Very preferably the group $-A^1-(Z^2-A^2)_m-$ is a group with one or two 5- or 6-membered rings.

Preferred subformulae for $-A-(Z^2-A^2)_m-$ are listed below. For reasons of simplicity, Phe in these groups is 1,4-phenylene, PheL is a 1,4-phenylene group which is substituted by 1 to 4 groups L as defined above, Cyc is 1,4-cyclohexylene, Pyd is pyridine-2,5-diyl and Pyr is pyrimidine-2,5-diyl. The following list of preferred groups $-A^1-(Z^2-A^2)_m-$ is comprising the subformulae II-1 to II-16 as well as their mirror images, -Phe-                II-1
-Pyd-                II-2
-Pyr-                II-3
-PheL-               II-4
-Cyc-                II-5
-Phe-Z-Cyc-          II-6
-Cyc-Z-Cyc-          II-7
-PheL-Cyc-           II-8
-Phe-Z-Phe-          II-9
-Phe-Z-Pyd-          II-10
-Pyd-Z-Phe-          II-11
-Phe-Z-Pyr-          II-12
-Pyr-Z-Phe-          II-13
-PheL-Z-Phe-         II-14
-PheL-Z-Pyd-         II-15
-PheL-Z-Pyr-         II-16
-Pyr-Z-Pyd-          II-17
-Pyd-Z-Pyd-          II-18
-Pyr-Z-Pyr-          II-19
-PheL-Z-PheL-        II-20

In these preferred groups Z has the meaning of $Z^1$ as given in formula I. Preferably Z is —COO—, —OCO—, —$CH_2CH_2$—C≡C— or a single bond.

Very preferably $-A^1-(Z-A^2)_m-$ is selected from the following formulae and their mirror images

 IIa

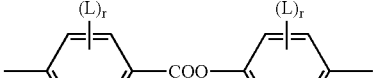 IIb

 IIc

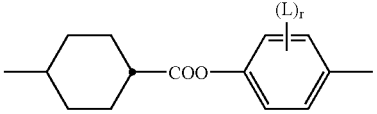 IId

 IIe

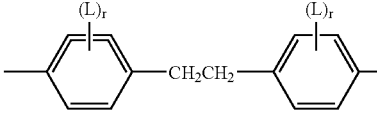 IIf

 IIg

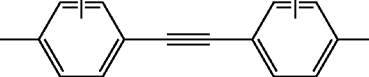 IIh

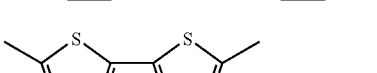 IIj

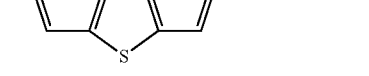 IIk

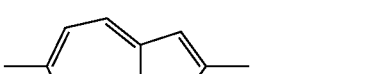 IIm

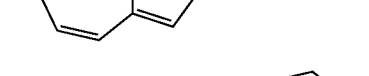 IIn wherein L has the meaning given above, $R^1$ is as defined for formula I and r is 0, 1, 2, 3 or 4, preferably 0, 1 or 2.

The group

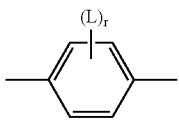

in these preferred formulae is very preferably Denotin

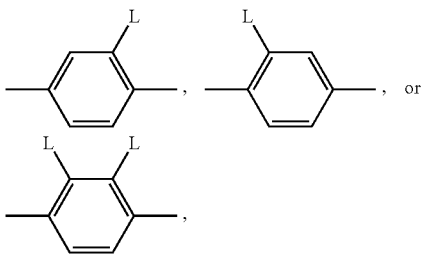

furthermore

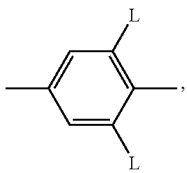

with L having each independently one of the meanings given above. Especially preferred compounds of formula I comprise at least one group

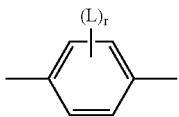

wherein r is 1.

Further preferred compounds of formula I comprise at least two groups

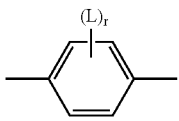

wherein r is 1 and/or at least one group

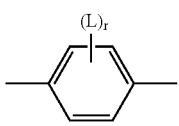

wherein r is 2.

If R is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

If R is an alkyl group wherein one or more $CH_2$ groups are replaced by —CH=CH—, this may be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1 E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

If R is an alkyl group, wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group R is straight-chain and has 2 to 6 C atoms.

It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

If R is an alkyl group, wherein two or more $CH_2$ groups are replaced by —O— and/or —COO—, it can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

If R is an alkyl or alkenyl group that is monosubstituted by CN or $CF_3$, it is preferably straight-chain. The substitution by CN or $CF_3$ can be in any desired position.

If R is an alkyl or alkenyl group that is at least monosubstituted by halogen, it is preferably straight-chain. Halogen is preferably F or Cl, in case of multiple substitution preferably F. The resulting groups include also perfluorinated groups. In case of monosubstitution the F or Cl substituent can be in any desired position, but is preferably in ω-position. Examples for especially preferred straight-chain groups with a terminal F substituent are fluormethyl, 2-fluorethyl, 3-fluorpropyl, 4-fluorbutyl, 5-fluorpentyl, 6-fluorhexyl and 7-fluorheptyl. Other positions of F are, however, not excluded.

Halogen means F, Cl, Br and I and is preferably F or Cl.

R can be a polar or a non-polar group. In case of a polar group, it is selected from CN, $SF_5$, halogen, $OCH_3$, SCN, $COR^5$, $COOR^5$ or a mono- oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of a non-polar group, it is preferably alkyl with up to 15 C atoms or alkoxy with 2 to 15 C atoms.

R can be an achiral or a chiral group. In case of a chiral group it is preferably selected of formula III:

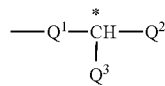

wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$ but being different from $Q^2$.

In case $Q^1$ in formula III is an alkylene-oxy group, the O atom is preferably adjacent to the chiral C atom.

Preferred chiral groups of formula III are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds containing an achiral branched group R may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

The polymerisable or reactive group P is preferably selected from $CH_2=CW^1$—COO—,

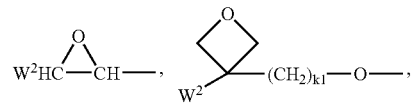

$CH_2=CW^2$—$(O)_{k1}$—, $CH_3$—CH=CH—O—, $(CH_2=CH)_2$CH—OCO—, $(CH_2=CH—CH_2)_2$CH—OCO—, $(CH_2=CH)_2$CH—O—, $(CH_2=CH—CH_2)_2$N—, HO—$CW^2W^3$—, HS—$CW^2W^3$—, $HW^2$N—, HO—$CW^2W^3$—NH—, $CH_2=CW^1$—CO—NH—, $CH_2=CH—(COO)_{k1}$-Phe-$(O)_{k2}$—, Phe-CH=CH—, HOOC—, OCN—, and $W^4W^5W^6Si$—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferably P is a vinyl group, an acrylate group, a methacrylate group, an oxetane group or an epoxy group, especially preferably an acrylate or methacrylate group.

As for the spacer group Sp all groups can be used that are known for this purpose to those skilled in the art. The spacer group Sp is preferably of formula Sp'-X, such that P-Sp- is P-Sp'-X—, wherein Sp' is alkylene with up to 20 C atoms which may be unsubstituted, mono- or poly-substituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—COO—, —OCO—CH=CH— or a single bond, and $R^0$, $R^{00}$, $Y^1$ and $Y^2$ have one of the meanings given above.

X is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=CR⁰—, —CY¹=CY²—, —C≡C—
or a single bond, in particular —O—, —S—, —C≡C—,
—CY¹=CY²— or a single bond, very preferably a group
that is able to from a conjugated system, such as —C≡C—
or —CY¹=CY²—, or a single bond.

Typical groups Sp' are, for example, —(CH$_2$)$_p$—,
—(CH$_2$CH$_2$O)$_q$—CH$_2$CH$_2$—, —CH$_2$CH$_2$—S—CH$_2$CH$_2$—
or —CH$_2$CH$_2$—NH—CH$_2$CH$_2$— or —(SiR⁰R⁰⁰—O)$_p$—,
with p being an integer from 2 to 12, q being an integer from
1 to 3 and R⁰ and R⁰⁰ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

In another preferred embodiment Sp' is a chiral group of formula IV:

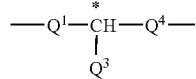

IV wherein

Q¹ and Q³ have the meanings given in formula III, and

Q⁴ is an alkylene or alkylene-oxy group with 1 to 10 C atoms or a single bond, being different from Q¹, with Q¹ being linked to the polymerizable group P.

Further preferred are compounds with one or two groups P-Sp- wherein Sp is a single bond.

In case of compounds with two groups P-Sp, each of the two polymerisable groups P and the two spacer groups Sp can be identical or different.

Particularly preferred compounds of formula I are those of the following formulae Ia

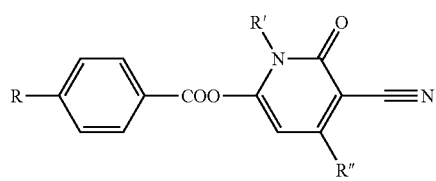

Ib

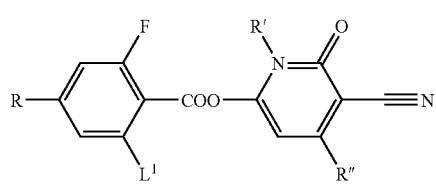

Ic

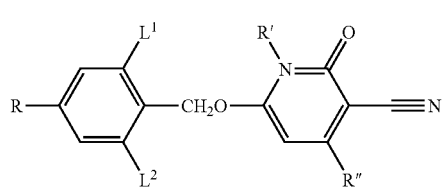

Id

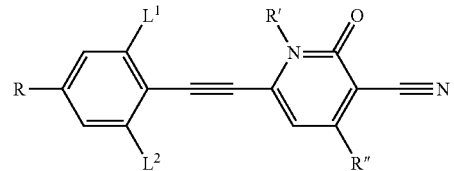

Ie

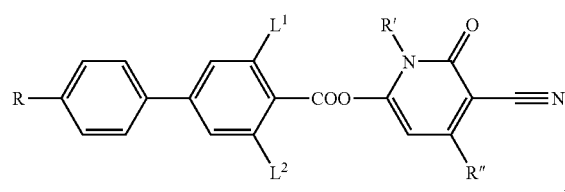

If

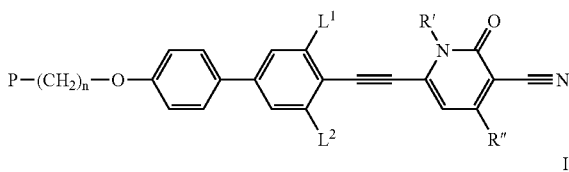

Ig

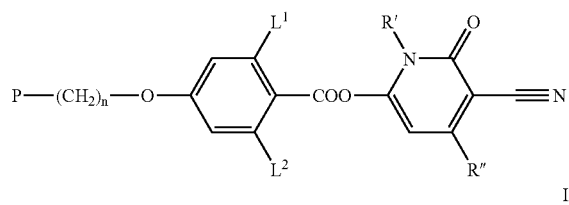

Ih

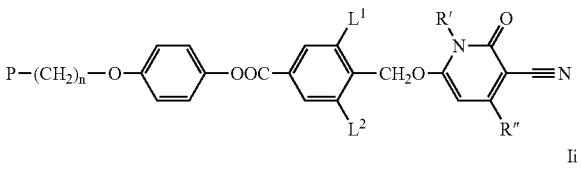

Ii

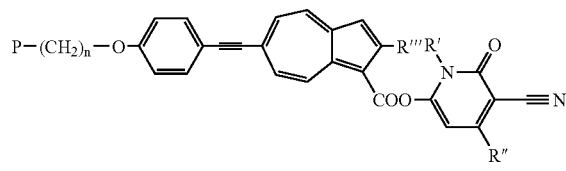

Ik

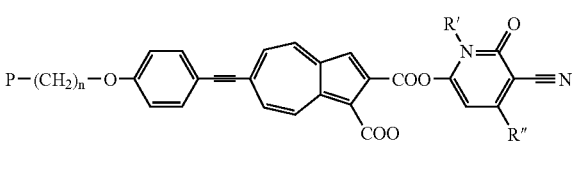

wherein

R has one of the meanings of formula I and is preferably straight chain alkyl, alkoxy with 1 to 8 C-atoms or alkenyl, alkenyloxy or alkinyl with 2 to 7 C-atoms, R' has one of the meanings of R¹ in formula I and is preferably H or alkyl with 1, 2 or 3 C-atoms, very preferably H, methyl or ethyl, R" has one of the meanings of R¹ in formula I and is preferably H or alkyl with 1, 2 or 3 C-atoms, very preferably H, methyl or ethyl, R'" has one of the meanings of $R^1$ in formula I and is preferably H or alkyl alkoxy with 1, 2 or 3 C-atoms, very preferably H, methyl(oxy) or ethyl(oxy), P has one of the meanings given above and below, $L^1$ and $L^2$ are independently of each other H or F, and n is an integer from 1 to 12.

The aromatic rings in the above preferred formulae are optionally substituted with 1, 2 or 3 groups L as defined above.

The compounds of formula I can be synthesized according to or in analogy to methods which are known per se and which are described in standard works of organic chemistry such as, for example, Houben-Weyl, Methoden der organischen Chemie, Thieme-Verlag, Stuttgart. Some specific and preferred methods are described in the reaction schemes below. Further methods can be taken from the examples.

Scheme 1:

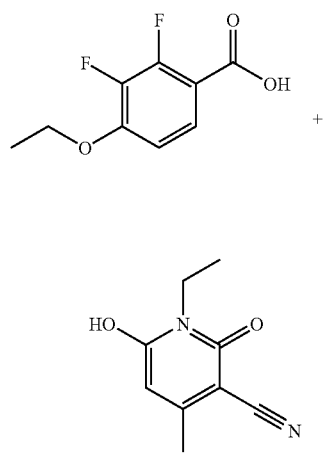

-continued

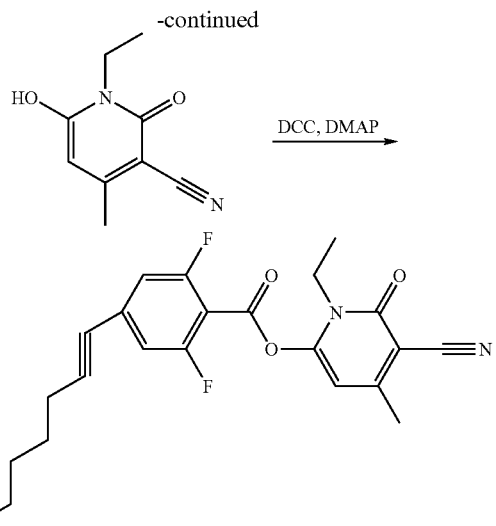

Scheme 3:

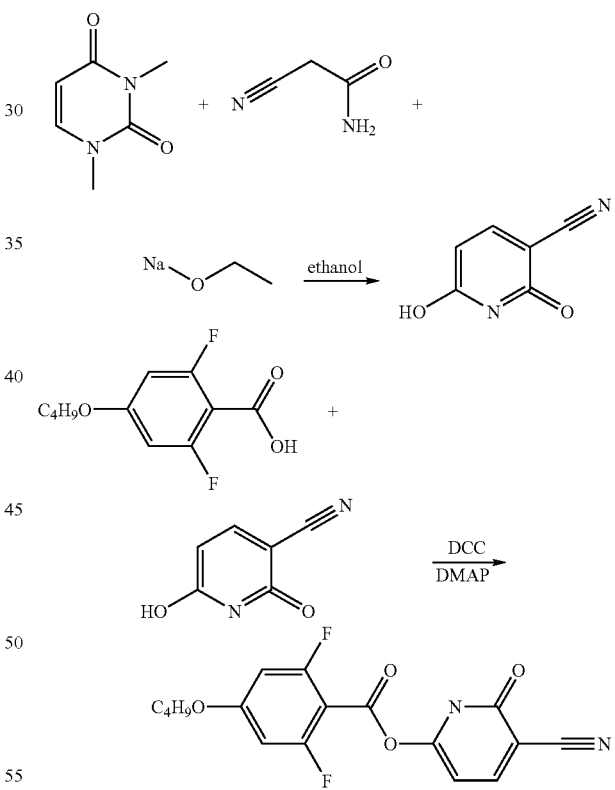

Scheme 2:

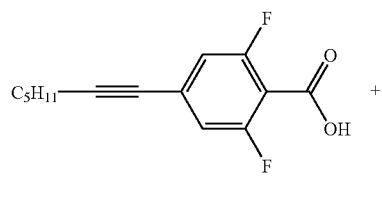

Scheme 4:

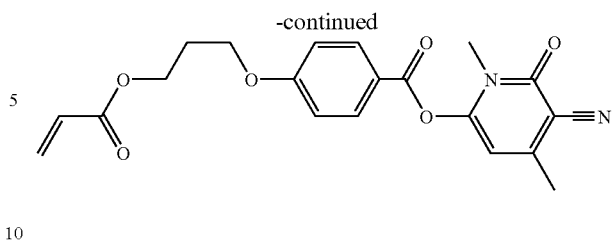

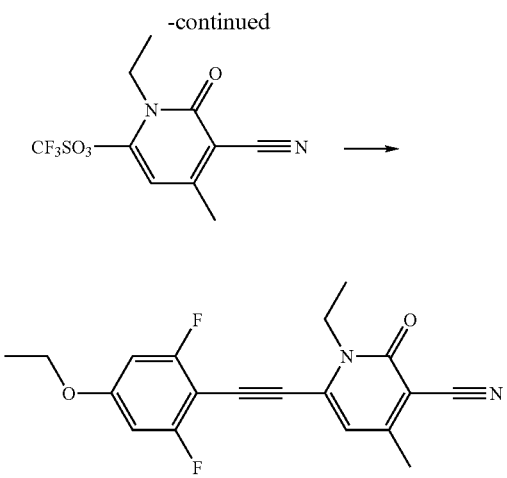

Scheme 5:

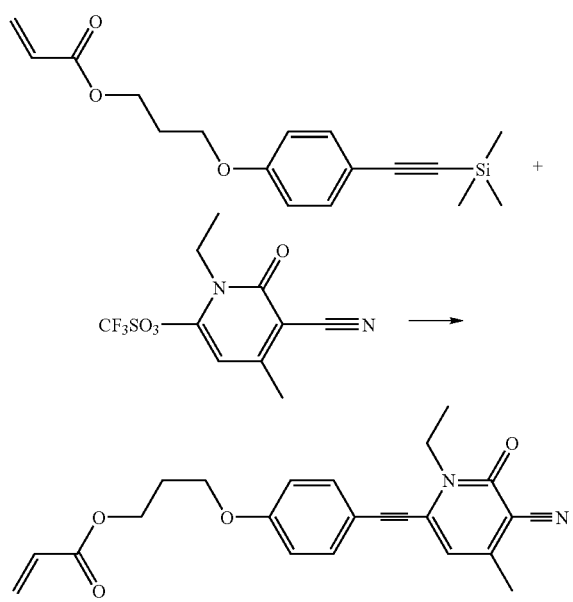

Scheme 6:

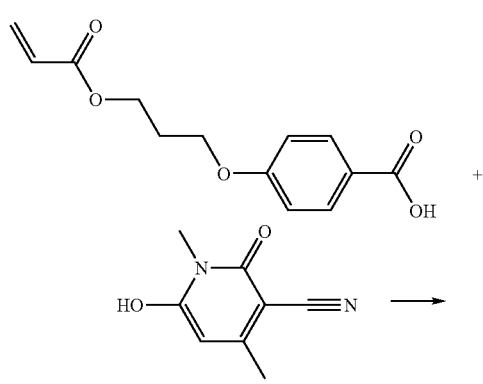

For the applications described above the LC media preferably contain at least one compound of formula 1, and a nematic host mixture comprising one or more nematic or nematogenic compounds.

Preferably the LC media consist of 2 to 25, preferably 3 to 15 compounds, at least one of which is a compound of formula I or I1. The other compounds, forming the nematic host mixture, are preferably low molecular weight liquid crystal compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexyl-biphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclohexylpyridazines, phenyl- or cyclohexyldioxanes, phenyl- or cyclo-hexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The most important compounds that are possible as components of these LC mixtures' can be characterized by the following formula

R'-L'-G'-E-R"

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

Examples of suitable polymerisable mesogenic compounds that can be used as comonomers together with the compounds of formula I in a polymerisable LC mixture, are disclosed for example in WO 93/22397, EP 0 261 712, DE 195 04 224, WO 95/22586, WO 97/00600 and GB 2 351 734. The compounds disclosed in these documents, however, are to be regarded merely as examples that shall not limit the scope of this invention.

Preferably the polymerizable LC mixture comprises at least one polymerisable mesogenic compound having one polymerisable functional group and at least one polymerisable mesogenic compound having two or more polymerisable functional groups.

Examples of especially useful chiral and achiral polymerisable mesogenic comonomers are shown in the following lists which should, however, be taken only as illustrative and is in no way intended to restrict, but instead to explain the present invention:

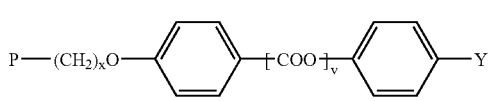
(Va)

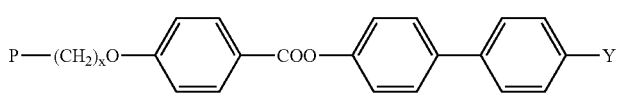
(Vb)

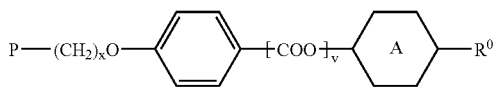
(Vc)

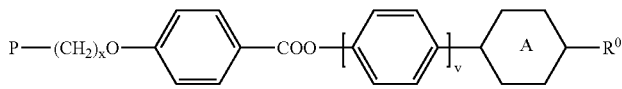
(Vd)

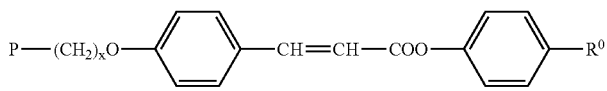
(Ve)

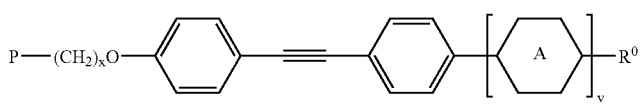
(Vf)

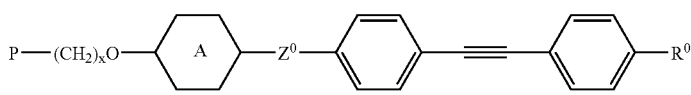
(Vg)

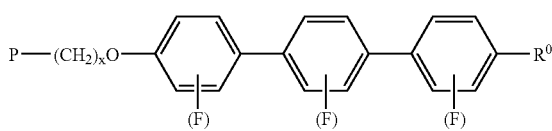
(Vh)

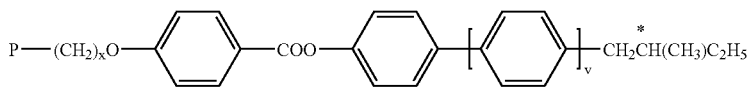
(Vi)

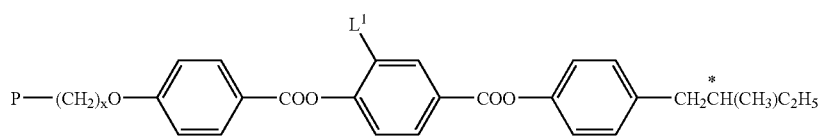
(Vk)

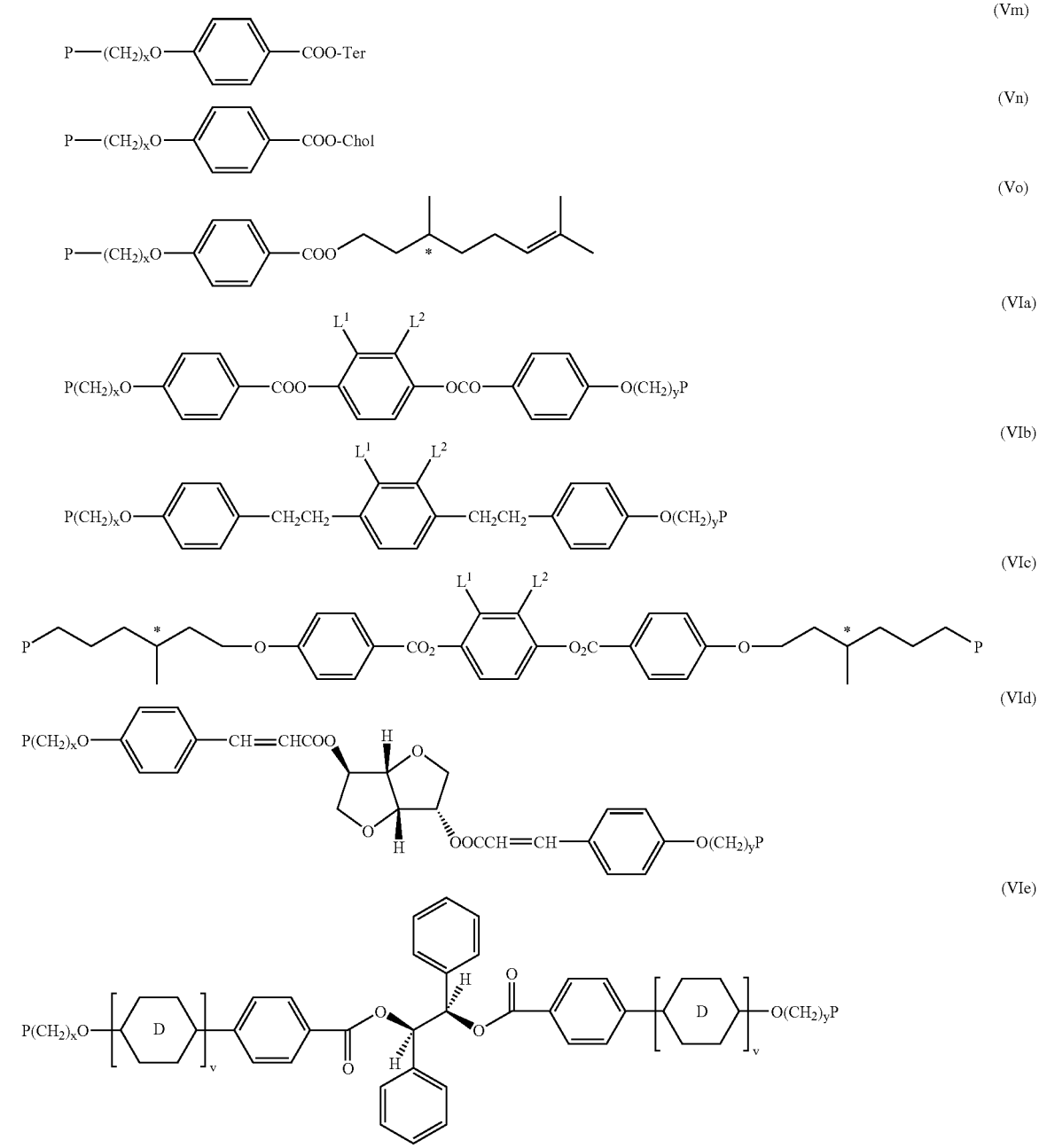

wherein P has one of the meanings of formula I and its preferred meanings as mentioned above, x and y are identical or different integers from 1 to 12, A and D are 1,4-phenylene or 1,4-cyclohexylene, v is 0 or 1, Y is a polar group, $R^0$ is a non-polar (or unpolar) alkyl or alkoxy group, Ter is a terpenoid radical like e.g. menthyl, Chol is a cholesteryl group, the phenylene rings in formulae Va to Vlc may also be substituted by 1, 2, 3 or 4 groups $L^1$, in particular mono- or difluorinated, and $L^1$ and $L^2$ are each independently H, F, Cl, OH, CN, $NO_2$ or optionally alkyl, alkoxy, alkylcarbonyl or alkoxycarbonyl with 1 to 7 C atoms.

The term 'polar group' in this connection means a group selected from F, Cl, CN, $NO_2$, OH, $OCH_3$, OCN, SCN, an optionally fluorinated carbonyl or carboxyl group with up to 4 C atoms or a mono-, oligo- or polyfluorinated alkyl or alkoxy group with 1 to 4 C atoms. The term 'non-polar group' (or 'unpolar group') means an alkyl group with 1 or more, preferably 1 to 12 C atoms or an alkoxy group with 2 or more, preferably 2 to 12 C atoms.

The polymerisable LC mixtures according to the present invention may also comprise one or more non-reactive chiral dopants in addition or alternatively to chiral polymerisable mesogenic compounds. Typically used chiral dopants are e.g. the commercially available R or S 811, R or S 1011, R or S 2011 or CB 15 (from Merck KGaA, Darmstadt, Germany). Very preferred are chiral dopants with a high helical twisting power (HTP), in particular dopants comprising a sorbitol group as described in WO 98/00428, dopants comprising a hydrobenzoin group as described in GB 2,328,207, chiral binaphthyl derivatives as described in WO 02/94805, chiral binaphthol acetal derivatives as described in WO 02/34739, chiral TADDOL derivatives as described in WO 02/06265, and chiral dopants with at least one fluorinated linkage group and a terminal or central chiral group as described in WO 02/06196 and WO 02/06195.

To prepare anisotropic polymer films, the polymerisable LC mixture is preferably coated onto a substrate, aligned and polymerised in situ, for example by exposure to heat or actinic radiation, to fix the orientation of the LC molecules. Alignment and curing are carried out in the LC phase of the mixture. This technique is well-known in the art and is generally described for example in D. J. Broer, et al., Angew. Makromoli. Chem. 183, (1990), 45-66.

Alignment of the LC material can be achieved for example by treatment of the substrate onto which the material is coated, by shearing the material during or after coating, by application of a magnetic or electric field to the coated material, or by the addition of surface-active compounds to the LC material. Reviews of alignment techniques are given for example by 1. Sage in "Thermotropic Liquid Crystals", edited by G. W. Gray, John Wiley & Sons, 1987, pages 75-77, and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerisable materials with acrylate or methacrylate groups, preferably a radical photoinitiator is used, when curing polymerisable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerisable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The examples below serve to illustrate the invention without limiting it. In the foregoing and the following, all temperatures are given in degrees Celsius, and all percentages are by weight, unless stated otherwise. The following abbreviations are used to illustrate the liquid crystalline phase behaviour of the compounds: K=crystalline; N=nematic; S=smectic; N*, Ch=chiral nematic or cholesteric; I=isotropic. The numbers between these symbols indicate the phase transition temperatures in degree Celsius.

EXAMPLE 1

Compound (1) was prepared as shown in reaction scheme 1 above.

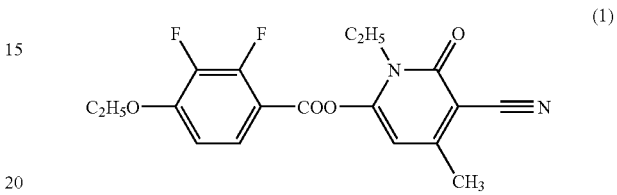

2,3-Difluoro-4-ethoxybenzoic acid (4.00 g, 0.02 mol), 1-ethyl-1,2-dihydro-6-hydroxy-4-methyl-2-oxo-3-pyridinecarbonitrile (commercially available from Aldrich) (3.56 g, 0.02 mol) and DCC (4.12 g, 0.02 mol) and a catalytic amount of dimethylaminopyridine in dimethylacetamide (80 ml) were charged to a 3- neck round bottomed flask and stirred under nitrogen at 35 degrees. Reaction progress was monitored by GCMS. After over night stirring, a precipitate of DCU was removed by filtration. The dimethylacetamide solvent was removed by distillation and the residue was partitioned between water and DCM. The chlorinated phase was washed, dried and evaporated. The crude product was purified by flash column chromatography using DCM as eluant. A solid was isolated, GCMS and NMR showed expected signals.

The compound has a melting point of 136° C.

EXAMPLE 2

Compound (2) was prepared as shown in reaction scheme 2 above.

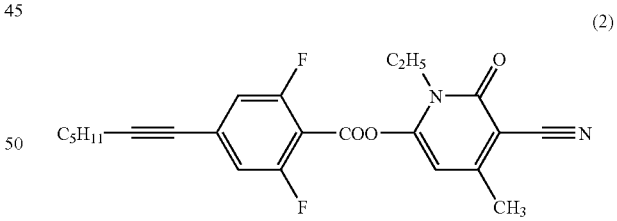

2,6-Difluoro-4-heptynylbenzoic acid (5.00 g, 0.02 mol), 1-ethyl-1,2-dihydro-6-hydroxy-4-methyl-2-oxo-3-pyridinecarbonitrile (3.56 g, 0.02 mol) and DCC (4.12 g, 0.02 mol) and a catalytic amount of dimethylaminopyridine in dimethylacetamide (80 ml) were charged to a 3-neck round bottomed flask and stirred under nitrogen at 35 degrees. Reaction procedure was monitored by TLC. After 16 h, TLC showed the reaction to have gone to completion. A white precipitate was removed by filtration. The filtrate was washed with water. The toluene phase was removed, dried over sodium sulphate and evaporated to dryness on a rotary evaporator. Purification was achieved by flash column chromatography using DCM as eluant. Evaporation of the appropriate fractions gave the desired product as a grey solid. (1 spot by TLC). ¹H NMR and GCMS showed expected signals.

The compound has a melting point of 98° C.

EXAMPLE 3

Compound (3) was prepared as shown in reaction scheme 3 above.

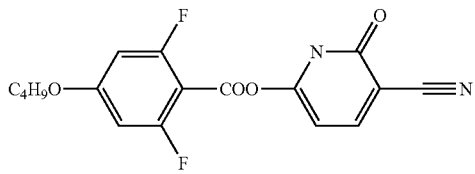

Dimethyluracil (10.0 g, 0.071 mol), 2-cyanoacetamide (5.97 g, 0.071 mol) and sodium ethoxide (9.66 g, 0.142 mol) were stirred in ethanol (300 ml). After 30 min a large amount of solid precipitate appeared. The precipitate was removed by filtration and recrystallised form hot water. A white solid was isolated and used without further purification in the next step.

4-Butyloxy-2,6-difluorobenzoic acid (9.43 g, 0.041 mol), 3-hydroxy-6-cyanopyrid-5-one (5.6 g, 0.041 mol), DCC (8.46 g, 0.041 mol) and a catalytic amount of dimethylaminopyridine in dimethylacetamide (100 ml) were charged to a 3-neck round bottomed flask and stirred under nitrogen at 35 degrees. Reaction progress was monitored by GCMS. After 16 h, the mixture was cooled, filtered to remove DCU and then distilled to remove dimethylacetamide. The residue was partitioned between water and ethyl acetate, the organic phase was removed, dried and evaporated to dryness. Purification was achieved by recrystallisation from ethyl acetate. GCMS showed expected signals.

The invention claimed is:

1. A liquid crystalline medium, comprising at least two liquid crystalline compounds, wherein at least one of said compounds comprises a 5-cyanophridon-2-yl group is of formula I

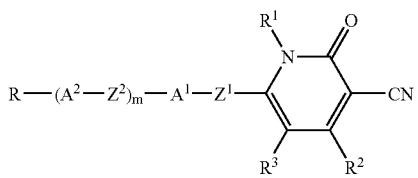

wherein $R^1$, $R^2$ and $R^3$ are independently of each other H or an optionally substituted aliphatic, cycloaliphatic or aromatic group with up to 20 C atoms that optionally comprises one or more hetero atoms and optionally comprises fused rings, $A^1$ and $A^2$ are independently of each other an aromatic or alicyclic ring, or a group comprising two or more fused aromatic or alicyclic rings, wherein these rings optionally contain one or more hetero atoms selected from N, O, and S, and are optionally mono- or polysubstituted by R, $Z^1$ and $Z^2$ are independently of each other —O—, —S—, —CO—, —COO—, —OCO—, —S—CO—, —CO—S—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, $Y^1$ and $Y^2$ are independently of each other H, F, Cl or CN, R is H, F, Cl, Br, I, CN, NO₂, NCS, SF₅ or alkyl which is straight chain or branched, has 1 to 20 C-atoms, is unsubstituted, mono- or poly-substituted by F, Cl, Br, I or CN, and in which one or more non-adjacent CH₂ groups are optionally replaced, in each case independently from one another, by —O—, —S—, —NH—, NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, or R denotes P-Sp R⁰ and R⁰⁰ are independently of each other H or alkyl with 1 to 12 C-atoms, P is a polymerisable or reactive group, Sp is a spacer group or a single bond, and m is 0, 1 or 2.

2. A cyanopyridone compound of formula I,

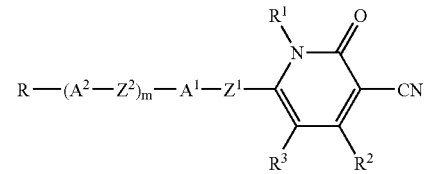

wherein $R^1$, $R^2$ and $R^3$ are independently of each other H or an optionally substituted aliphatic, cycloaliphatic or aromatic group with up to 20 C atoms that optionally comprises one or more hetero atoms and optionally comprises fused rings, $A^1$ and $A^2$ are independently of each other an aromatic or alicyclic ring, or a group comprising two or more fused aromatic or alicyclic rings, wherein these rings optionally contain one or more hetero atoms selected from N, O and S, and are optionally mono- or polysubstituted by R, $Z^1$ and $Z^2$ are independently of each other —O—, —S—, —CO—, —COO—, —OCO—, —S—CO—, —CO—S—, —O—COO—, —CO—NR⁰—, —NR⁰—CO—, —OCH₂—, —CH₂O—, —SCH₂—, —CH₂S—, —CF₂O—, —OCF₂—, —CF₂S—, —SCF₂—, —CH₂CH₂-, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, $Y^1$ and $Y^2$ are independently of each other H, F, Cl or CN, R is H, CN, NO₂, NCS, SF₅ or alkyl which is straight chain or branched, has 1 to 20 C-atoms, is unsubstituted, mono- or poly-substituted by F, Cl, Br, I or CN, and in which one or more non-adjacent CH₂ groups are replaced, in each case independently from one another, by —S—, —NH—, —NR⁰—, —SiR⁰R⁰⁰—, —CO—, —COO—, —OCO—, —OCO—O—, —S—CO—, —CO—S—, —CY¹=CY² or —C≡C— in such a manner that O and/or S atoms are not linked directly to one another, or R denotes P-Sp, R⁰ and R⁰⁰ are independently of each other H or alkyl with 1 to 12 C-atoms, P is a polymerisable or reactive group, Sp is a spacer group or a single bond, and m is 0, 1 or 2, with the proviso that if m is 0, $R^1$ and $R^3$ are H, $R^2$ is carboxyethyl and $Z^1$ is CH=CH, CH=C(CH₃) or CH=C(C₆H₅), then $A^1$—R is different from phenyl or 4-methoxyphenyl.

3. A cyanopyridone compound according to claim 2, wherein $A^1$ and $A^2$ are furane-2,5-diyl, thiophene-2,5-diyl, thienothiophene-2,5-diyl, dithienothiophene-2, 6-diyl, pyrrol-2,5-diyl, 1,4-phenylene, azulene-2,6-diyl, pyridine-2,5-diyl, pyrimidine-2,5-diyl, naphthalene-2,6-diyl, 1,2,3,4-tetrahydronaphthalene-2,6-diyl, indane-2,5-diyl, or 1,4-cyclohexylene wherein one or two non-adjacent CH₂ groups are optionally replaced by O and/or S, and wherein $A^1$ and $A^2$ are each independently unsubstituted, mono- or polysubstituted by L, wherein L is CN, NO₂, or by an alkylcarbonyl or alkoxycarbonyl group with 1 to 12 C atoms, wherein one or more H atoms are optionally replaced by F or Cl.

4. A cyanopyridone compound according to claim 2, wherein $Z^1$ is —O—, —COO—, —OCO—, —OCOO—, —CH₂O—, —OCH₂—, —CF₂O—, —OCF₂—, —C≡C— or —CH=CH—.

5. A cyanopyridone compound according to claim 2, wherein —$A^1$—($Z^2$—$A^2$)$_m$— is

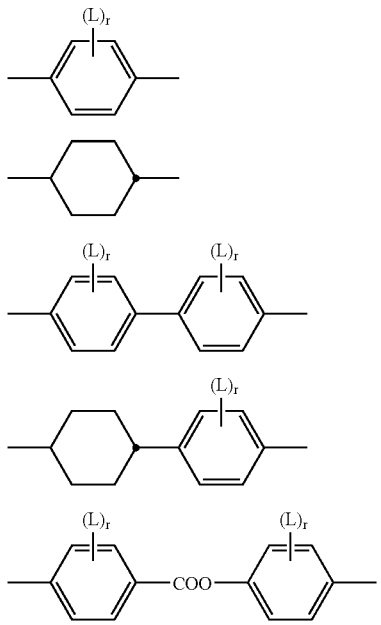

IIa

IIb

IIc

IId

IIe

-continued

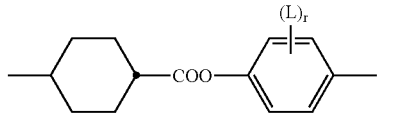

IIf

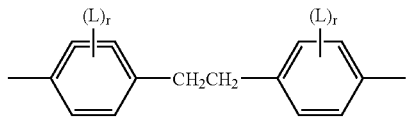

IIg

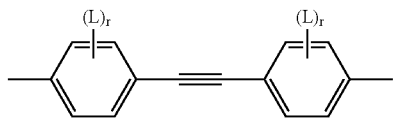

IIh

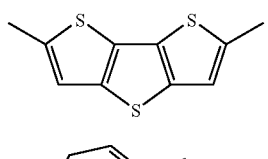

IIj

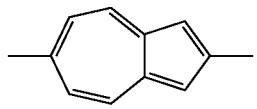

IIk

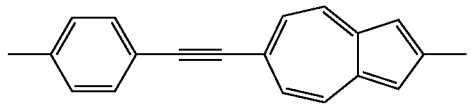

IIm

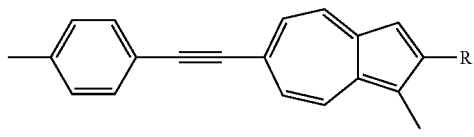

IIn

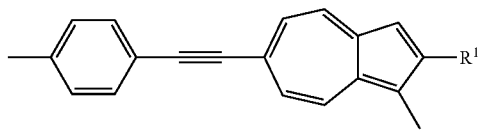

or a mirror image thereof, wherein L is CN, NO₂, or an alkylcarbonyl or alkoxycarbonyl group with 1 to 12 C atoms, wherein one or more H atoms are optionally replaced by F or Cl, and r is 0, 1, 2, 3 or 4.

6. A cyanopyridone compound according to claim 2, wherein R is P-Sp.

7. cyanopyridone compound according to claim 2, wherein R is alkyl or alkoxy with 1 to 12 or alkenyl, alkenyloxy or alkynyl with 2 to 12 C-atoms.

8. A cyanopyridone compound according to claim 2, of the formula

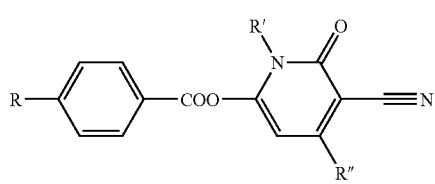

Ia

-continued
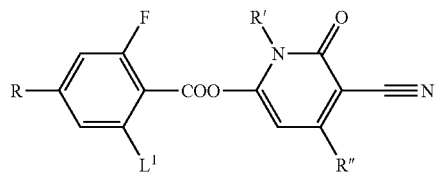
Ib
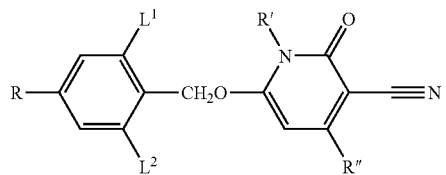
Ic
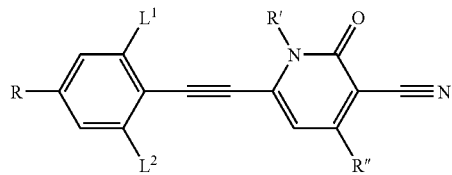
Id
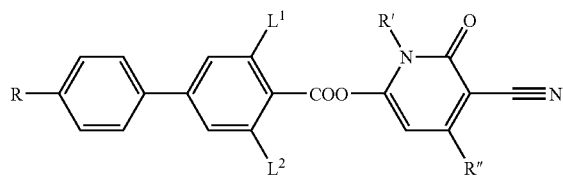
Ie
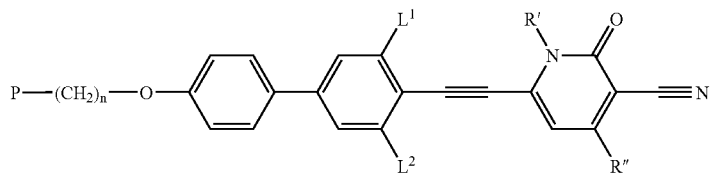
If
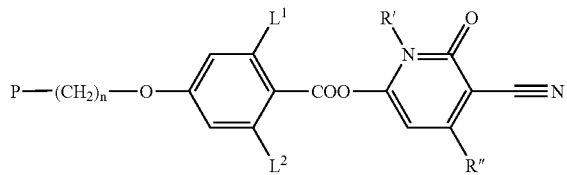
Ig
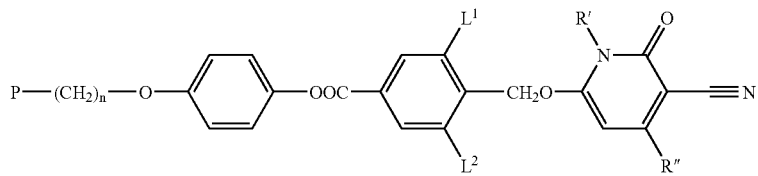
Ih
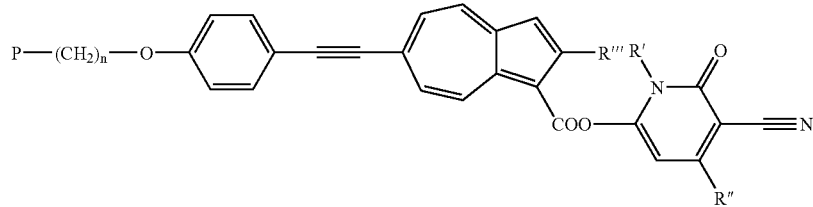
Ii -continued

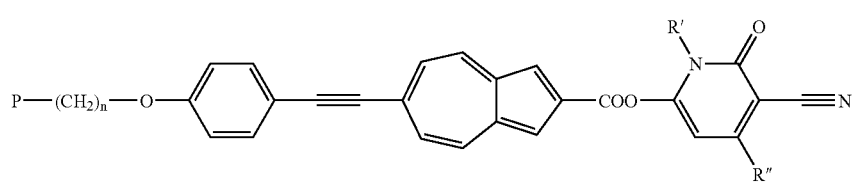
Ik or a mirror image thereof,
wherein
R″ and R‴ each independently have one of the meanings of $R^1$ in formula I,
P is a polymerisable or reactive group,
$L^1$ and $L^2$ are independently of each other H or F, and
n is an integer from 1 to 12.

9. A liquid crystal medium according to claim 1, comprising at least one polymerisable compound, which can be said cyanopyridone compound of formula I or an additional compound.

10. A polymer obtained by polymerizing a cyanopyridone compound according to claim 4.

11. In electrooptical displays, liquid crystal displays, optical films, polarisers, compensators, beam splitters, reflective films, alignment layers, colors filters, holographic elements, hot stamping foils, colored images, decorative or security markings, LC pigments, adhesives, synthetic resins with anisotropic mechanical properties, cosmetics, pharmaceutics, diagnostics, nonlinear optics, optical information storage, chiral dopants, electronic devices, components of integrated circuitry, thin film transistors in flat panel display applications, Radio Frequency Identification (RFTD) tags, semiconducting components for organic light emitting diode (OLED) applications, electroluminescent displays, backlights of LCDs, photovoltaic or sensor devices, batteries, photoconductors, or electrophotographic recording media comprising a liquid crystalline medium, the improvement wherein the medium is one according to claim 1.

12. An electrooptical device, comprising a liquid crystal medium, according to claim 1.

13. The liquid crystal device according to claim 12, which is a TN or STN display or a display using liquid crystals in the isotropic phase.

14. A polymer obtained by polymerizing a liquid crystalline medium according to claim 9.

15. A polymer according to claim 10, which polymer is anisotropic.

16. A polymer according to claim 14, which polymer is anisotropic.

17. A cyanopyridone compound of formula I,

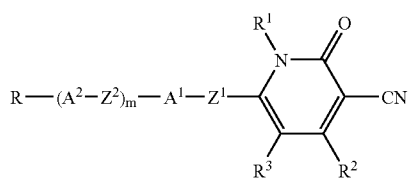
I wherein $R^1$, $R^2$ and $R^3$ are independently of each other H or an optionally substituted aliphatic, cycloaliphatic or aromatic group with up to 20 C atoms that optionally comprises one or more hetero atoms and optionally comprises fused rings, $A^1$ and $A^2$ are independently of each other an aromatic or alicyclic ring, or a group comprising two or more fused aromatic or alicyclic rings, wherein these rings optionally contain one or more hetero atoms selected from N, O and S, and are optionally mono- or polysubstituted by R, $Z^1$ $Z^2$ are independently of each other —O—, —S—, —CO—,
—COO—, —OCO—, —S—CO—, —CO—S—, —O—COO—, —CO—$NR^0$—,
—$NR^0$—CO—, —$OCH_2$—, —$CH_2O$—, —$SCH_2$—, —$CH_2S$—, —$CF_2O$—,
—$OCF_2$—, —$CF_2S$—, —$SCF_2$—, —$CH_2CH_2$—, —$CF_2CH_2$—,
—$CH_2CF_2$—, —$CF_2CF_2$—, —CH=N—, —N=CH—, —N=N—,
—CH=$CR^0$—, —$CY^1$=$CY^2$—, —C≡C—, —CH=CH—COO—, —OCO—CH=CH— or a single bond, $Y^1$ and $Y^2$ are independently of each other H, F, Cl or CN,
R is H, CN, $NO_2$, NCS, $SF_5$ or P-Sp,
$R^0$ and $R^{00}$ are independently of each other H or alkyl with 1 to 12 C-atoms,
P is a polymerisable or reactive group,
Sp is a spacer group or a single bond, and
m is 0, 1 or 2.

18. The liquid crystalline medium according to claim 1, wherein R is H, CN, $NO_2$, NCS, $SF_5$ or alkyl which is straight chain or branched, has 1 to 20 C-atoms, is unsubstituted, mono— or poly-substituted by F, Cl, Br, I or CN, and in which one or more non-adjacent $CH_2$ groups are replaced, in each case independently from one another, by —S—, —NH—, —$NR^0$—, —$SiR^0R^{00}$—, —CO—, —COO—, —OCO—, —OCO—O—,
—S—CO—, —CO—S—, —$CY^1$=$CY^2$— or —C≡C— in such a manner that O and/or S atoms are not linked directly to one another, or R denotes P-Sp.

19. The liquid crystalline medium according to claim 1, wherein R is H, CN, $NO_2$, NCS, $SF_5$ or P-Sp.

* * * * *

UNITED STATES PATENT AND TRADEMARK OFFICE
CERTIFICATE OF CORRECTION

PATENT NO. : 7,442,475 B2
APPLICATION NO. : 10/546146
DATED : October 28, 2008
INVENTOR(S) : Louise Diane Farrand It is certified that error appears in the above-identified patent and that said Letters Patent is hereby corrected as shown below:

On the front page, Inventors: line 1, reads "Dorset" should read -- Blandford Forum --

Column 25, line 40, reads "group is of" should read -- group of --

Column 26, line 16, reads "—C=C—" should read -- —C≡C— --

Column 26, line 18, reads "denotes P-Sp" should read -- denotes P-Sp, --

Column 26, line 54, reads "—C=C—" should read -- —C≡C— --

Column 26, line 60, reads "F, CI, Br," should read -- F, Cl, Br, --

Column 26, line 65, reads "—C=C—" should read -- —C≡C— --

Column 28, compound IIg: line 10, reads " 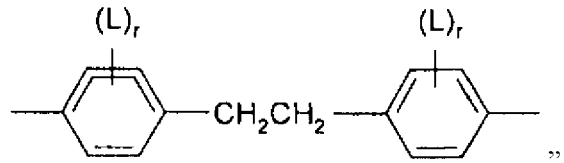 "

should read -- 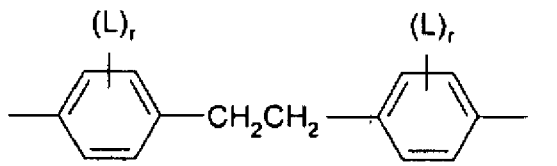 --

Column 28, line 49, reads "cyanopyridone" should read -- A cyanopyridone --

Column 28, line 50, reads "1 to 12 or" should read -- 1 to 12 C-atoms or --

Column 31, line 24, reads "according to claim 4." should read -- according to claim 2. --

Column 31, line 27, reads "colors filters," should read -- color filters, --

Column 31, line 30-31, reads "pharmaceutics," should read -- pharmaceuticals, --

CERTIFICATE OF CORRECTION (continued)
U.S. Pat. No. 7,442,475 B2

Column 31, line 34, reads "(RFTD)" should read -- (RFID) --

Column 32, line 25, reads "$Z^1$ $Z^2$" should read -- $Z^1$ and $Z^2$ --

Column 32, line 36, reads "—C=C—" should read -- —C≡C— --

Column 32, line 56, reads "—C=C—" should read -- —C≡C— --

Signed and Sealed this

Fifth Day of January, 2010

David J. Kappos
*Director of the United States Patent and Trademark Office*